United States Patent [19]
Halverson et al.

[11] Patent Number: 5,874,217
[45] Date of Patent: Feb. 23, 1999

[54] MICROSATELLITE SEQUENCES FOR CANINE GENOTYPING

[75] Inventors: Joy Halverson; Jan Dvorak; Tamara Stevenson, all of Davis, Calif.

[73] Assignee: The Perkin-Elmer Corporation, Foster City, Calif.

[21] Appl. No.: 623,906

[22] Filed: Mar. 27, 1996

[51] Int. Cl.⁶ .............................. C12Q 1/68; C12P 19/34; C07H 21/02; C07H 21/04

[52] U.S. Cl. ............................ 435/6; 435/91.2; 536/23.1; 536/24.3; 536/24.33

[58] Field of Search ...................... 435/6, 91.2; 536/23.1, 536/24.3, 24.33

[56] References Cited

PUBLICATIONS

Shibuya et al., "Two Polymorphic Microsatellites in a Coding Segment of the Canine Androgen Receptor Gene," *Animal Genetics* 24:345–348 (1993).

Fredholm et al., "Variation of Short Tandem Repeats Within and Between Species Belonging to the Canidae Family," *Mammalian Genome* 6:11–18 (1995).

Zajc et al., "A New Method of Paternity Testing for Dogs, Based on Microsatellite Sequences," *The Veterinary Record* 135: 545–547 (Dec. 3, 1994).

Francisco et al. Mammalian Genome 7(5) 359–362, 1996.

Rothuisen et al. theoretical. Appli. Gene. 89: 403–406, 1994.

Edwards et al. Amer. J. of Human Genet 49: 746–756, 1991.

Primmer te al. Anim. Genet 24:332, 1993.

*Primary Examiner*—W. Gary Jones
*Assistant Examiner*—Dianne Rees
*Attorney, Agent, or Firm*—Scott R. Bortner

[57] ABSTRACT

Methods of genotyping canines by analysis of polymorphisms in the number of microsatellite DNA repeats are provided. The internal repeat sequence is amplified by the use of specific primers. The number of repeats, and therefore the distance between the primers, is highly variable in a population, thereby providing an allelic marker for the locus. The combined information from multiple loci provides a means of distinguishing individuals, even among inbred dog breeds, for parentage testing, forensic testing and analysis of individuals relatedness.

18 Claims, No Drawings

MICROSATELLITE SEQUENCES FOR CANINE GENOTYPING

TECHNICAL FIELD

The field of this invention is canine genotyping.

BACKGROUND

The increased ability to analyze the genetic makeup of individuals from different species has allowed a number of new techniques to be developed. Detection of genetic polymorphisms is useful for differentiating between individuals, parentage testing, forensic testing, analysis of relatedness of individuals, and mapping genes of interest linked to the microsatellite repeats.

Microsatellites are perfect, imperfect, or compound arrays of tandemly repeated nucleotide sequences embedded in an otherwise unique nucleotide sequence. Microsatellite repeats typically range from one to six base pairs (bp) in length. The microsatellite repeat arrays vary in the number of repeats from 6 to 30 or more in humans. However, the longer arrays of repeats are less frequently isolated. Microsatellites may consist of simple repeats containing only one uninterrupted repeated sequence, imperfect repeats containing two identical repeats separated by a small interval of non-repeated nucleotides, or compound repeats containing several different repeated sequence types (Weber, 1990). For an individual, any particular microsatellite chromosomal locus may vary in the number of repeats present.

Commonly used methods of genetic mapping by microsatellites take advantage of length variations among individuals (Weber and May, 1989). Utilizing the nucleotide sequence of the cloned microsatellite and its flanking regions, oligonucleotide primers for the PCR are designed that anneal to unique sequences that flank the repeats. The primers can be designed as near or far from the microsatellite as desired, the only limit being the resulting size of the PCR product for subsequent analysis.

Detection and size determination of PCR products from a specific microsatellite locus can be accomplished by several means. As the procedure was first described, PCR products are labeled with $^{32}P$, fractionated by a denaturing polyacrylamide gel electrophoresis and visualized by autoradiography. Alternatively, the PCR products are labeled with a fluorochrome, and separated on an automated DNA sequencing apparatus. Another method separates the PCR products by capillary electrophoresis, which has the advantage of being much faster than acrylamide gel electrophoresis while maintaining the accuracy of sizing (Buttler et al., infra.).

Whichever method is used for sizing of the DNA fragments, there is a limit to the resolution that is achieved. It becomes more difficult to obtain resolution of 1–2 bp when the fragments sized are greater than 500 bp, since the size difference between the products as a percentage of the total fragment size is small. Therefore, PCR primers must be designed such that the products of the reaction are easily distinguished from each other and accurately sized. Primers are usually designed to generate PCR products of 50 to 500 bp. In the future, methods may be developed to accurately resolve fragments of 1 Kb or even greater.

To date, many polymorphic dinucleotide microsatellites, usually of the (CA)n motif, have been isolated from the canine genome (Holmes et al., 1993; Ostrander et al., 1993). However, few polymorphic microsatellites other than those based on dinucleotide motifs have been isolated. There are several difficulties associated with the use of microsatellites based on dinucleotide motifs. One problem is the inherent difficulty of reproducible sizing, due to the high resolution required to accurately determine the size of PCR products derived from dinucleotide repeats. Another obstacle is the presence of so-called "stutter" bands generated due to slipped-strand mispairing during PCR, which is especially noticeable when employing microsatellites with dinucleotide motifs. These artifactual bands, which appear at 2 bp intervals below the correct size band, can make determination of allele size difficult in many cases.

Based on the inherent difficulties in typing with dinucleotide repeats, there is interest in determining trinucleotide and tetranucleotide repeat polymorphisms. Characterization of such polymorphisms may be useful in automation and standardized genotyping.

Relevant Literature

Construction of a genetic linkage map in man using restriction fragment length polymorphisms is described in Botstein et al. (1980) *Amer. J. Hum. Genet.* 32: 314–331. DNA typing and genetic mapping with trimeric and tetrameric tandem repeats is described in Edwards et al. (1991) *Amer. J. Hum. Genet.* 49: 746–756. The informativeness of human (dC-dA)n.(dG-dT)n polymorphisms is discussed in Weber (1990) *Genomics* 7: 524–530.

Intrageneric amplification of horse microsatellite markers with emphasis on the Przewalski's horse is disclosed in Breen et al. (1994) *Anim. Genet.* 25:401–405. Marklund et al. (1994) Anim. Genet. 25: 19–23, describe parentage testing and linkage analysis in horse using a set of highly polymorphic microsatellites.

Holmes and Sampson (1993) Anim. Genet. 24: 289–292 describe the isolation and characterization of microsatellites from the canine genome. Shibuya et al. (1993). *Anim. Genet.* 24: 245–348 describes polymorphic microsatellites in a coding segment of the canine androgen receptor gene. Ostrander et al. 1993 *Genomics* 16:207–213, identify and characterize dinucleotide repeat (CA)n markers for genetic mapping of dog. Primmer and Matthews (1993) *Anim. Genet.* 24:332, identify canine tetranucleotide repeat polymorphism at the VIAS-D10 locus. Shibuya et al. (1994) *Anim. Genet.* 25:122 describe a polymorphic (AGGAAT)n tandem repeat in an intron of the canine von Willebrand factor gene. The efectivness of using co-dominant polymorphic allelic series for checking pedigrees and distinguishing full-sib pair members is discussed in Jamieson (1994) *Anim. Genet.* 25: 37–44.

Rapid analysis of a short tandem repeat by capillary electrophoresis is described in Buttler et al. (1994) *BioTechniques* 17:1062–1070. Hague and Litt (1993) *Hum. Mol. Genet.* 2:411–415, study the origin of 'shadow bands' seen when typing dinucleotide repeat polymorphisms by the PCR. Knowles et al. (1992) *Amer. J. Hum. Genet.* 51:905–909 describe techniques in gene mapping with microsatellite markers. Moore et al. (1991) Genomics, 10: 654–660 describe the use of heterologous PCR primer pairs in closely related species. Weber and May (1989) *Amer. J.*

Hum. Genet. 44: 388–396, describe an abundant class of human DNA polymorphisms which can be typed using the polymerase chain reaction. Ziegle et al. (1992) *Genomics* 14:1026–1031 provide an application of automated DNA sizing technology for genotyping microsatellite loci.

SUMMARY OF THE INVENTION

Methods and compositions are provided for performing diagnostic assays on canine species for differentiation between individuals, parentage testing, forensic testing, analysis of relatedness of individuals, and for mapping genes of interest. Unique canine DNA sequences having internal trinucleotide and tetranucleotide microsatellite repeats are polymorphic markers that can be easily assayed for differences between individuals. Detection of these polymorphisms allows genotyping analysis to be performed.

DESCRIPTION OF THE SPECIFIC EMBODIMENTS

Methods are provided for genotyping canines by analysis of polymorphisms in the number of microsatellite DNA repeats. Oligonucleotide primers complementary to the regions flanking the repeats are used to amplify the internal repeat sequence. The number of repeats, and therefore the distance between the primers, is highly variable in a population. The length polymorphism from a single locus may be used for mapping genes of interest. Specific primers and sequences of microsatellite loci are provided, where the loci have a high PIC value in canine populations. The combined information from multiple loci provides a means of distinguishing individuals, even among inbred dog breeds, for parentage testing, forensic testing and analysis of individuals relatedness.

Microsatellite loci that are useful in the subject methods will have the general formula:

$U(R)_n U'$, where

U and U' are non-repetitive flanking sequences that uniquely identify the particular locus, R is a repeat motif, and n is the number of repeats. The locus will be present on a canine chromosome. Specific examples are provided in the Sequence Listing, SEQ ID NO: 1 through SEQ ID NO:20.

The repeat motif will be at least 3 nucleotides in length, preferably 4 nucleotides in length. The internal sequence may be a simple repeat, such as $(R)_n$, or may be a complex repeat, such as $(R)_n(R')_{n'}(R)_n(R')_{n'}(R)_n(R')_{n'}(R)_n(R')_{n'}(R'')_{n'''}$, etc. In some complex repeats, one or more of the motifs may be as long as six nucleotides. The motif sequence will generally consist of three A or three T residues, with the fourth residue being any one of G, C, A or T. Specific repeat sequences having this formula include AAAG; GAAA; AAAT; TTTC; CTTT; and TTTA. Other repeat motifs are AAGG, GAAT; GAAG; GAAAA; AAAAAG; TGC and TTC.

The flanking sequences U and U' uniquely identify the microsatellite locus within the canine genome. U and U' will be at least about 18 liucleotides in length, and may extend a distance of several thousand bases. The DNA having U and U' sequences may be obtained in substantial purity as restriction fragments, amplification products, etc., and will be obtained as a sequence other than a sequence of an intact chromosome. Usually, the DNA will be obtained substantially free of other nucleic acid compounds which do not include a microsatellite sequence or fragment thereof, generally being at least about 50%, usually at least about 90% pure and are typically "recombinant", i.e. flanked by one or more nucleotides with which they are not normally associated with on a natural chromosome.

Within the flanking sequences U and U', sequences will be selected for amplification primers, P and P'. The exact composition of the primer sequences are not critical to the invention, but they must hybridize to the flanking sequences U and U', respectively, under stringent conditions. Conditions for stringent hybridization are known in the art, for example one may use a solution of 5×XSSC and 50% formamide, incubated at 42° C. To maximize the resolution of size differences at the locus, it is preferable to chose a primer sequence that is close to the repeat sequence, usually within at least about 100 nt of the repeat, more usually at least about 50 nt, and preferably at least about 25 nt. Algorithms for the selection of primer sequences are generally known, and are available in commercial software packages. The primers will hybridize to complementary strands of chromosomal DNA, and will prime towards the repeat sequences, so that the repeats will be amplified. The primers will usually be at least about 18 nt in length, and usually not more than about 35 nt in length. Primers may be chemically synthesized in accordance with conventional methods or isolated as fragments by restriction enzyme digestion, etc.

The number of repeats at a specific locus, n, will be polymorphic in a population, thereby generating individual differences in the length of DNA that lies between U and U'. The number will vary from at least 1 repeat to as many as about 150 repeats. Useful markers for genotyping are polymorphic in the population to be tested. The polymorphism at a particular microsatellite locus is proportional to the variance in the values for n in the population. The PIC value is corresponds to allele frequency. The formula for calculating PIC is as follows:

$$PIC = 1 - \left( \sum_{i=1}^{n} Pi^2 \right) - \sum_{i=1}^{n-1} \sum_{j=i+1}^{n} 2pi^2pj^2$$

where pi and pj are allele frequencies, and n is the number of alleles. The PIC value of a microsatellite locus used in the subject method will be at least about 0.35 for the population to be tested, usually at least about 0.5 for the population.

The family Canidae includes the species, dogs, wolves, coyotes, foxes and jackals. The degree of homology between these species is high, and in most cases the subject methods can be used with any canine species. Various subpopulations, such as dog breeds, isolated wild populations, etc. may be highly inbred. Inbred populations have a reduced number of polymorphic loci, as compared to an outbred population. It is convenient to analyze multiple loci, and where a particular microsatellite locus is insufficiently informative within the population, e.g. having a PIC value of less than about 0.25 for the population in question, the data from that locus will not be included in the final determination of genotype.

Genomic DNA is isolated from the individual or individuals that are to be tested. DNA can be isolated from any nucleated cellular source such as blood, hair shafts, saliva, mucous, biopsy, feces, etc. Amplification can be performed on the DNA from a single cell, although it is convenient to use at least about $10^5$ cells.

The primers are used to amplify the region of genomic DNA that contains the repeats. Amplification may use the polymerase chain reaction, ligase chain reaction, etc. Suitable reaction conditions for PCR are described in Saiki, et al. (1985) *Science* 239:487, and Sambrook, et al. *Molecular Cloning: A Laboratory Manual*, CSH Press 1989, pp.14.2–14.33. Useful thermostable polymerases known in the art include those isolated from *Thermus aquaticus, Thermococcus litoralis, Pyrococcus furiosis*, and *Thermus thermophilus*. A description of ligase chain reaction (LCR) may be found in International patent application WO 9302215.

Conveniently, a detectable label will be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescrin (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high afifnity binding partner, e.g. avidin, specific antibodies, etc., where the binding partner is conjugated to a detectable label. The label may be conjugated to one or both of the primers. Alternatively, the pool of nucleotides used in the amplification may be labeled, so as to incorporate the label into the amplification product.

Multiplex amplification may be performed in which several sets of primers are combined in the same reaction tube. This is particularly advantageous when limited amounts of sample DNA are available for analysis. Conveniently, each of the sets of primers will be labeled with a different fluorochrome.

After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) *Science* 254:59–74. The automated sequencer is particularly useful with multiplex amplification. Capillary electrophoresis may also be used for fractionation. A review of capillary electrophoresis may be found in Landers, et al. (1993) *BioTechniques* 14:98–111.

The size of the amplification product is proportional to the number of repeats (n) that are present at the locus specified by the primers. The size will be polymorphic in the population, and is therefore an allelic marker for that locus. For many applications, a panel of loci will be analyzed, usually at least about 5, more usually at least about 10. The combined information for the panel of loci serves as a "DNA fingerprint" for the individual.

The DNA fingerprint allows for identification of lost or stolen animals and confirmation of identity, such as may be required for show or stud dogs. Genotypes can be compared to assess the degree of relatedness between two individuals. Individuals that are closely related have a higher probability of shared alleles than unrelated individuals (see Chakraborty and Lin (1993) *Hum. Biol.* 65:875–895; and Hammond (1994) *Am. J. Hum. Genet.* 55:175–189). Knowledge of relatedness is useful for the improvement of breeding programs, and for increasing genetic diversity in a population. Canine DNA samples recovered from crime scenes may be used to provide forensic evidence.

The genotypes are useful for parentage testing. Individuals can be ruled out as possible sires or dams of an offspring in question by comparing their genotypes. Each individual must receive one allele from its mother and one from its father at each locus, so that putative parents that do not share an allele at every locus with the individual in question can be excluded from parentage. When using a set of microsatellite markers for parentage testing, it is important to know how powerful they are in terms of detection of false parentage. The formula for parentage exclusion (PE) states the probability that a given series of codominant alleles should detect a falsely recorded parent, Jamieson (1994) *Anim. Genet.* 25:37–44. The PE can be calculated for each locus, and for all of the loci combined.

Other uses of the subject methods include mapping genes of interest, e.g. genes controlling hereditary diseases, desirable traits, etc. that are genetically linked to the marker loci. Isolation and mapping of many microsatellite markers can be used to construct a genetic map of the dog genome; this map will aid in elucidation of the genetics of morphology and behavior in dog breeds and in understanding genetic diseases common to humans and dogs. Those involved in conservation efforts may utilize genotype information to maximize genetic diversity in species of limited population size.

A kit may be provided for practice of the subject methods. Such a kit will contain at least one set of specific primers useful for amplifying microsatellite DNA repeats, and preferably will have a panel of primers. The primers may be conjugated to a detectable marker, usually a panel of four primers will have four different labels to facilitate multiplex amplification. In a preferred embodiment, the panel of primers will be selected from those described in the experimental section, SEQ ID NO:21 to SEQ ID NO:60.

The following examples are offered by way of illustration and not by way of limitation.

EXPERIMENTAL

Genomic DNA isolation and Library Construction

Genomic DNA isolation: One testicle weighing approximately 5 grams from a domestic dog was frozen in liquid nitrogen and ground to a fine powder using a mortar and pestle Thirty ml extraction buffer (10 mM Tris 8.0, 0.1M EDTA 8.0, 20 mg/ml RNAse A, and 0.5% SDS) was added to the ground tissue in a sterile 50 ml conical centrifuge tube. The tube was mixed well and incubated for 30 minutes at 37° C. Proteinase K was added to final concentration of 100 mg/ml, mixed and incubated for 3 hours on a rocking platform at 50°–55° C. The tube was then cooled to room temperature and five extractions with an equal volume of phenol: chloroform: isoamyl alcohol (1:1:24) were performed. One-tenth of the volume and 2 volumes of 3M sodium acetate and 95% ethanol were added, respectively. The solution was mixed well and DNA was recovered onto a glass rod. The DNA was washed in 70% ethanol and resuspended in TE by rocking overnight at 50°–55° C.

Library Construction: Ten mg of canine genomic DNA was digested to completion with AluI. The digested DNA was fractionated in a 2% low melting point agarose gel and fragments from 200–500 bp were gel purified and ligated to pBluescriptSK+ (Stratagene, La Jolla Calif.), which had been digested with SmaI and treated with calf intestinal alkaline phosphatase. The ligations were carried out in a volume of 10 ml at 15° C. overnight. Ligations were heated for 15 minutes at 75° C., and the plasmid was ethanol precipitated, dried, and resuspended in water. The ligation was then digested with SmaI to eliminate vector background. Top10F' competent cells (Invitrogen, San Diego Calif.) were then transformed by electroporation and plated onto 15 large Petri plates. The resulting genomnic library contained 472,000 primary recombinants. The library was stored as a glycerol stock.

Library Screening: Small aliquots of the glycerol stock of the library were diluted 1:10⁶ or a: 10⁷ in LB media plus ampicillin (100 mg/ml). Fifty ml of the diluted library was plated out. Individual colonies were selected and transferred onto 9 cm Petri plates at a density of 100 per plate. Two replica plates were made of each plate for screening. Colonies were lifted from each of the two replica plates onto nitrocellulose membranes (S&S, Keene NH). Each membrane was placed colony side up in approximately three ml of denaturant solution (0.5M NaOH, 1.5M NaCl) on a sheet of Saran Wrap for five minutes, then transferred to the same amount of neutralization solution (0.5M Tris, 1.5M NaCl, pH 7.0) for five minutes, and finally was placed in a solution of 2xSSC and rocked gently for five minutes. The filters were then rubbed gently to remove excess debris and blotted dry on Whatman 3 mm paper prior to being baked at 80° C. for one hour. They were then exposed to UV light for two minutes and were prehybridized in 6xSSPE, 5xDenhardt's and 0.2% SDS for at least 30 minutes at 60° C. End labeled probes were then added for hybridization overnight at 60° C. The oligonucleotides labeled for use as probes (BIOS Laboratories, New Haven Conn.) were as follows: (AAG)9, (AAC)9, (AAT)12, (AAAC)7A, (AAAG)7A, and (AAAT)9. The filters were hybridized with one of the above probes at a time for ready identification of microsatellite repeat motifs. After hybridization, filters were washed once at room temperature for 15 minutes in 6xSSPE and 0.2% SDS, and then washed twice at 60° C. for 15 minutes each time in 6xSSPE and 0.2% SDS. Filters were wrapped in Saran Wrap and exposed to X-ray film overnight at −80° C. Colonies hybridizing with a probe were selected and plasmid DNAs were isolated.

Sequencing of Positive Clones and PCR Primer Design: Plasmid DNA was isolated using the Qiagen tip-20 kit (Qiagen, Chatsworth Calif.), and DNA was sequenced on an Applied Biosystems 373A Stretch Automated Sequencer using the PRISM Dye Deoxy Terminator Sequencing Kit (Perkin Elmer, Norwalk Conn.). PCR primers flanking the microsatellite repeat in each clone were designed so as to produce amplified DNA ranging from 75 to 350 bp. Primers were synthesized by Operon Technologies (Alameda, Calif.), and in each case, one primer was end labeled with one of three fluorescent dyes (FAM, JOE, or TAMRA) while the other primer was not labeled. The primer pairs had the following sequences:

| Locus | Primer 1 | | Primer 2 | |
|---|---|---|---|---|
| 1 | SEQ ID NO:21 | CACTTCTCATACCCAGACTC | SEQ ID NO:41 | CAATATGTCAACTATACTTC |
| 2 | SEQ ID NO:22 | ATGAGCACTGGGTGTTATAC | SEQ ID NO:42 | ACACAATTGCATTGTCAAAC |
| 3 | SEQ ID NO:23 | ATCCTGGAGACCTGGGATTG | SEQ ID NO:43 | GATTGAGTCATCAATAGATG |
| 4 | SEQ ID NO:24 | TATCGACTTTATCACTGTGG | SEQ ID NO:44 | ATGGAGCCTCATGTCTCATC |
| 5 | SEQ ID NO:25 | ACGCCTGAACTTAATCCTGG | SEQ ID NO:45 | ACAGTTATCCAACAATGAGG |
| 6 | SEQ ID NO:26 | GCTATCTTGTTTCCCACAGC | SEQ ID ND:46 | TCACTGTATACAACATTGTC |
| 7 | SEQ ID NO:27 | CCTGCCTTTGTAAATGTAAG | SEQ ID NO:47 | CTTCATTGAAGTATCTATCC |
| 8 | SEQ ID NO:28 | ATTCTCTGCCTCTCCCTTTG | SEQ ID ND:48 | TGTGGATAATCTCTTCTGTC |
| 9 | SEQ ID NO:29 | TCTAGTCCCCAGTCTAGTTCACTGCCC | SEQ ID NO:49 | AGTCTGGTGATTTAATTCGG |
| 10 | SEQ ID NO:30 | CCTAAATTAGAGGTCTAACC | SEQ ID NO:50 | TAAGCGGGAATGTGCTCCTC |
| 11 | SEQ ID NO:31 | CTCAGCACCGAGTCTGCTTG | SEQ ID NO:51 | CCTGTTCTAGGAACCCTATG |
| 12 | SEQ ID NO:32 | AACCGGTTGTGATTTCTGGG | SEQ ID NO:52 | TCTGTGTCATTAGTGACATC |
| 13 | SEQ ID NO:33 | TGGGGCTTAACTCCAAGTTC | SEQ ID NO:53 | CAGTACAGAGTCTGCTTATC |
| 14 | SEQ ID NO:34 | GCTCTTTGTAAAATGACCTG | SEQ ID NO:54 | TGGGAATCGTCCTAAAACCC |
| 15 | SEQ ID NO:35 | TTGCTCAGTGCTAAGTCTC | SEQ ID NO:55 | GACTCATGATGTTGTGTATC |
| 16 | SEQ ID NO:36 | CTAATGTGTCTCTCAAGCCG | SEQ ID NO:56 | TGGGGAGATCTACAGACCAC |
| 17 | SEQ ID NO:37 | GTAGATTAGATCTCAGGCAG | SEQ ID NO:57 | TAGGTCCTGGTAGGGTGTGG |
| 18 | SEQ ID NO:38 | GAGAAGATAAAGCAATTCTC | SEQ ID NO:58 | AAGTCATTAATCTCTCCTCG |
| 19 | SEQ ID NO:39 | GTGGAACCTGCTTAAGATTC | SEQ ID NO:59 | CTAAGGGACTGAACTTCTCC |
| 20 | SEQ ID NO:40 | GCCCTTGAATATGAACAATG | SEQ ID NO:60 | TCCTCTCTAACTGCCTATGC |

The designation of a locus in the tables corresponds to the sequence ID number, hence locus 1 has the sequence of SEQ ID NO:1, etc.

Assay of PCR Primers for Detection of Polymorphism: PCR was performed on canine genomic DNA using 10 pmol of each primer, 3 mM MgCl$_2$, 1X Perkin Elmer PCR buffer, 175 mM each dNTP (Pharmacia, Uppsala Sweden), and 1 unit of AmpliTaq DNA polymerase (Perkin Elmer, Norwalk Conn.) per 50 ml reaction. DNA was amplified in a Gene-Amp 9600 thermocycler (Perkin Elmer, Norwalk Conn.) for 1 minute at 94° C. followed by 30 cycles of 15 seconds at 94° C., 15 seconds at 58° C., and 30 seconds at 72° C., followed by a final extension of 72° C. for 10 minutes. One to five ml of PCR product was fractionated by size on a 6% denaturing acrylamnide gel (12 or 24 cm well-to-read) using an Applied Biosystems 373A Stretch Automated Sequencer. Genescan 350ROX markers (Perkin Elmer, Norwalk Conn.) were present in each lane as internal size standards. PCR products were sized using the Genescan software (Perkin Elmer, Norwalk Conn.) and genotype tables created with Genotyper software (Perkin Elmer, Norwalk Conn.).

Initially, 23 dogs of various breeds and a control plasmid containing the cloned microsatellite were amplified with each primer pair. Primer pairs that were promising in terms of polymorphism were assayed with DNAs of about 75 additional dogs in order to calculate allele frequencies in the dog population. Some of the primer pairs were used to assay a population of closely related German Shepherds for genetic polymorphism. The number and size range of alleles was tabulated, and observed heterozygosity (number of heterozygous dogs at a locus/total number of dogs analyzed) was calculated. PIC values were also calculated according to the formula given by Botstein et. al.

Procurement of Genomic DNA Samples from Individuals: DNA samples were obtained from either blood or buccal swab. DNA was isolated from blood using the QIAAMP™ Blood Kit (Qiagen, Chatsworth Calif.) according to the manufacturer's instructions. Five ml of the resulting DNA was used for each PCR reaction. DNA was isolated from buccal swabs taken by rubbing a commercially available cytology brush against the inside of the dog's cheek for 15 to 30 seconds. The swabs can be stored dry for several months in the paper wrapper before use. The head of the brush is placed in a one ml microtiter tube (Bio-Rad, Hercules Calif.) containing 600 ml 50 mM NaOH and the brush is swirled gently. The tube (with the brush still inside) is heated to 95° to 100° C. for five minutes. The brush is then carefully removed, and 60 ml of 1M Tris pH 8.0 is added to the tube. The tube is then vortexed and 5 ml of the DNA is used for each PCR reaction.

Analysis Of Canine Populations

Tables 1 and 2 demonstrate the utility of the PCR primers designed from the provided nucleotide sequences. The PIC value (Botstein et al. 1980) reveals the informativeness of each microsatellite. By the PIC value, 19 of the 20 markers presented are highly informative (PIC >0.5) and one is reasonably informative (0.25<PIC<0.5) in the general dog population (Table 1). In a population of closely related German Shepherds, nine markers were highly informative, eight were reasonably informative, and three markers were not very informative (Table 2). Observed heterozygosity is the fraction of dogs that were heterozygous for a specific marker. Nineteen of the twenty markers show an observed heterozygosity greater than 0.5, and ten of twenty display an observed heterozygosity greater than 0.7 in the general dog population (Table 1). In the German Shepherd population, eleven of the markers exhibit heterozygosity greater than 0.5, and five markers demonstrate heterozygosity greater than 0.7 (Table 2).

The data regarding the German Shepherd population were obtained from dogs owned by two local breeders who practice extensive line breeding, resulting in inbreeding and reduction of genetic variation. Despite this inbreeding, the majority of the claimed markers still display significant polymorphism between individuals. Therefore, these markers are useful for differentiating even very closely related individuals in the canine population.

TABLE 1

Characteristics of provided microsatellites at indicated canine loci in a population of dogs of various breeds.

| Locus | Number of Dogs | Number of Alleles | Observed Heterozygosity | PIC Value | Fragment Size in Base Pairs |
|---|---|---|---|---|---|
| 1 | 101 | 13 | 0.782 | 0.841 | 114–150 |
| 2 | 91 | 7 | 0.802 | 0.385 | 92–116 |
| 3 | 93 | 12 | 0.710 | 0.787 | 159–203 |
| 4 | 78 | 6 | 0.526 | 0.627 | 189–209 |
| 5 | 68 | 8 | 0.765 | 0.786 | 222–250 |
| 6 | 119 | 15 | 0.731 | 0.842 | 245–305 |
| 7 | 140 | 16 | 0.757 | 0.861 | 256–316 |
| 8 | 98 | 11 | 0.724 | 0.858 | 127–167 |
| 9 | 116 | 12 | 0.664 | 0.815 | 197–241 |
| 10 | 99 | 7 | 0.667 | 0.649 | 169–193 |
| 11 | 94 | 9 | 0.702 | 0.767 | 168–200 |
| 12 | 101 | 5 | 0.515 | 0.633 | 90–106 |
| 13 | 89 | 14 | 0.775 | 0.844 | 192–244 |
| 14 | 90 | 10 | 0.556 | 0.770 | 282–318 |
| 15 | 126 | 7 | 0.548 | 0.641 | 187–211 |
| 16 | 105 | 11 | 0.476 | 0.778 | 146–198 |
| 17 | 121 | 14 | 0.645 | 0.838 | 254–306 |
| 18 | 111 | 19 | 0.721 | 0.870 | 212–284 |
| 19 | 72 | 7 | 0.690 | 0.765 | 199–223 |
| 20 | 56 | 6 | 0.446 | 0.708 | 118–138 |

TABLE 2

Characteristics of provided microsatellites at indicated canine loci in a population of closely related German Shepherds.

| Locus | Number of Dogs | Number of Alleles | Observed Heterozygosity | PIC Value | Fragment Size in Base Pairs |
|---|---|---|---|---|---|
| 1 | 43 | 6 | 0.349 | 0.441 | 120–138 |
| 2 | 45 | 1 | 0 | 0 | 116 |
| 3 | 44 | 8 | 0.773 | 0.760 | 167–203 |
| 4 | 43 | 4 | 0.605 | 0.642 | 189–201 |
| 5 | 36 | 6 | 0.750 | 0.718 | 226–246 |
| 6 | 41 | 8 | 0.707 | 0.615 | 221–281 |
| 7 | 39 | 13 | 0.769 | 0.825 | 257–305 |
| 8 | 40 | 4 | 0.75 | 0.665 | 135–147 |
| 9 | 42 | 5 | 0.619 | 0.500 | 173–233 |
| 10 | 42 | 4 | 0.548 | 0.406 | 173–185 |
| 11 | 42 | 3 | 0.690 | 0.501 | 172–184 |
| 12 | 38 | 3 | 0.447 | 0.300 | 94–102 |
| 13 | 41 | 4 | 0.537 | 0.487 | 200–220 |
| 14 | 40 | 5 | 0.250 | 0.279 | 290–306 |
| 15 | 40 | 2 | 0.425 | 0.295 | 195–199 |
| 16 | 41 | 3 | 0.537 | 0.383 | 182–190 |

TABLE 2-continued

Characteristics of provided microsatellites at indicated canine loci in a population of closely related German Shepherds.

| Locus | Number of Dogs | Number of Alleles | Observed Heterozygosity | PIC Value | Fragment Size in Base Pairs |
|---|---|---|---|---|---|
| 17 | 43 | 2 | 0.023 | 0.023 | 274–278 |
| 18 | 41 | 5 | 0.390 | 0.391 | 232–284 |
| 19 | 41 | 2 | 0.244 | 0.191 | 211–215 |
| 20 | 42 | 4 | 0.19 | 0.527 | 111–135 |

An example of parentage testing in two families is shown below in Table 3. For ease of scoring genotypes, different letters have been assigned to each allele size at each locus. In the first family, parentage is not excluded since all offspring contain one allele present in the dam and the other allele is present in the sire. In the second family, there are two possible dams, one of which (Dam 2A) is excluded as the dam of the puppy in question at five loci (marked with an asterisk), since the puppy does not have any alleles in common with Dam 2A at those loci. However, Dam 2B is not excluded as the dam of the puppy, since the puppy shares one allele with the dam and one with the sire at each locus. In the general dog population, using the same allele frequencies used to calculate PIC values for Table 1, the probability of detection of falsely recorded parentage using all loci is 0.999999998. For the German Shepherd population in Table 2, the probability is 0.999613. These data indicate that these markers are quite powerful for parentage testing, since even in the population of very closely related German Shepherds, the likelihood of failing to detect false parentage is less than 1 in 1000.

TABLE 3

Parentage testing in two families of dogs

| | Family 1 | | | | | Family 2 | | | |
|---|---|---|---|---|---|---|---|---|---|
| Locus | Sire 1 | Dam 1 | Puppy 1A | Puppy 1B | Puppy 1C | Sire 2 | Dam 2A | Dam 2B | Puppy 2 |
| 1 | EE | BG | EG | EG | BE | BE | *EF | BB | BB |
| 2 | AC | AB | BC | BC | AB | AC | AB | BB | AB |
| 3 | DE | CD | CE | CE | CE | CD | *FG | CD | CD |
| 4 | AC | CH | AH | CH | CH | AD | AC | AC | CD |
| 5 | CE | CD | DE | CD | CD | CD | *AE | DE | DD |
| 6 | MQ | IN | NQ | MN | IQ | OO | MP | MO | MO |
| 7 | HK | FJ | FK | HJ | FH | JL | *II | IK | KL |
| 8 | DD | AA | AD | AD | AD | DF | *DD | CE | DE |

Genotyping a Wild Population

An illustration of the use of some of the markers for genotyping in Fennec foxes is presented in Table 4, below. Foxes A–D are from a wild population which may contain some siblings.

TABLE 4

Genotyping of Fennec foxes

| Locus | Fox A | Fox B | Fox C | Fox D |
|---|---|---|---|---|
| 1 | DE | DE | DE | DE |
| 2 | EF | EF | EF | EF |
| 3 | HH | HH | HH | HH |

TABLE 4-continued

Genotyping of Fennec foxes

| Locus | Fox A | Fox B | Fox C | Fox D |
|---|---|---|---|---|
| 4 | DF | FF | FF | FF |
| 5 | CH | CH | CH | CH |
| 6 | HW | HX | HH | HJ |
| 7 | JJ | JJ | JL | JL |
| 8 | EE | EE | EE | EE |

Although the foxes are remarkably similar genetically according to these markers, they can all be distinguished from each other using only eight markers. The genetic similarity may be due to a high degree of interrelatedness in this small sample size.

It is evident from the above results that the subject invention provides for a valuable means of genotyping canines. The microsatellite markers are informative even in highly inbred dog populations, and in wild canine populations. The genotyping provides a simple method of "finger- printing" an individual animal. Parentage analysis can be performed with the subject methods, as well as for gene mapping in canine populations.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of genotyping a canine at a microsatellite locus, the method comprising:
    amplifying with oligonucleotide primers specifically hybridizing to said locus, a region of chromosomal DNA, wherein said region of DNA comprises a repeated tetranucleotide motif consisting of AAA or TTT, with the fourth residue the tetranucleotide repeat motif being any one of G, C, A or T;
    size fractionating the product of said amplification to provide a measure of the size of chromosomal DNA between said primers;
    wherein said size of the product of the amplification is an polymorphic for said locus and, provides a genotype for said canine.

2. A method according to claim 1, wherein said amplifying further comprises labeling said product with a detectable label.

3. A method according to claim 2, wherein said amplifying comprises performing the polymerase chain reaction.

4. A method according to claim 3, wherein a panel of at least about 5 of said microsatellite loci are genotyped, and wherein said allelic markers for said loci provide a genetic fingerprint for the identification of said canine.

5. A method of genotyping a canine at a microsatellite locus, the method comprising:
    amplifying with oligonucleotide primers specifically hybridizing to said locus, a region of chromosomal DNA, wherein said region of DNA comprises a repeated motif selected from the group consisting of AAAG, GAAA, AAAT, TTTC, CTTT, TTTA, AAGG, GAAT, GAAG, GAAAA, AAAAAG, TGC and TTC;
    size fractionating the product of said amplification to provide a measure of the size of chromosomal DNA between said primers;
    wherein said size of the product of the amplification is polymorphic for said locus and provides a genotype for said canine.

6. A method according to claim 5, wherein said amplifying further comprises labeling said product with a detectable label.

7. A method according to claim 6, wherein said amplifying uses the polymerase chain reaction.

8. A method according to claim 7, wherein a panel of at least about 5 said microsatellite loci are genotyped, and wherein said allelic markers for said loci provide a genetic fingerprint for the identification of said canine.

9. A method according to claim 8, wherein said oligonucleotide primers specifically hybridizing to said locus are selected from the group consisting of SEQ ID NO:21 and 41; 22 and 42; 23 and 43; 24 and 44; 25 and 45; 26 and 46; 27 and 47; 28 and 48; 29 and 49; 30 and 50; 31 and 51; 32 and 52; 33 and 53; 34 and 54; 35 and 55; 36 and 56; 37 and 57; 38 and 58; 39 and 59; and 40 and 60.

10. A composition comprising an isolated DNA fragment, wherein the sequence of said DNA is selected from the group consisting of SEQ ID NO:1 through SEQ ID NO:20.

11. An oligonucleotide primer of at least about 18 nucleotides in length, wherein said primer is capable of specifically hybridizing to a DNA having the sequence of the flanking regions of the group consisting of SEQ ID NO:1 through SEQ ID NO:20.

12. An oligonucleotide primer according to claim 11, wherein the sequence of said primer is selected from the group consisting of SEQ ID NO:21 through SEQ ID NO:60.

13. A kit for use in genotyping canines, comprising:
   a pair of oligonucleotide amplification primers, wherein the sequence of said primers is selected from the flanking regions of the group consisting of SEQ ID NO:1 through SEQ ID NO:20.

14. A kit according to claim 13, wherein at least one of said primers is conjugated to a detectable label.

15. A kit according to claim 14, wherein said detectable label is a fluorochrome.

16. A kit according to claim 15, wherein said kit comprises a panel of at least about 5 of said pairs of oligonucleotide amplification primers.

17. A kit according to claim 16, wherein the sequence of said oligonucleotide amplification primers is selected from the group consisting of SEQ ID NO:21 and 41; 22 and 42; 23 and 43; 24 and 44; 25 and 45; 26 and 46; 27 and 47; 28 and 48; 29 and 49; 30 and 50; 31 and 51; 32 and 52; 33 and 53; 34 and 54; 35 and 55; 36 and 56; 37 and 57; 38 and 58; 39 and 59; and 40 and 60.

18. A method according to claim 5, wherein the amplification primers can specifically hybridize to flanking regions from the group consisting of SEQ ID NO:1 through SEQ ID NO:20.

* * * * *

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..28
        ( D ) OTHER INFORMATION: /note= "Nucleotides 1-28 are unique
            flanking sequence"

( i x ) FEATURE:
        ( A ) NAME/KEY: misc_feature
        ( B ) LOCATION: 29..103
        ( D ) OTHER INFORMATION: /note= "Nucleotides 29-103 are
            repeat sequence"

( i x ) FEATURE:
        ( A ) NAME/KEY: misc_feature
        ( B ) LOCATION: 104..252
        ( D ) OTHER INFORMATION: /note= "Nucleotides 104-252 are
            unique flanking sequence"

( x i ) SEQUENCE DESCRIPTION: SEQ ID NO:1:

```
CCCTCACTTC  TCATACCCAG  ACTCCTCGCT  GCTGCTGCTG  CTGCTGCTTC  TTCTTCTTCT       60

TCTTCTTCTT  CTTCTTCTTC  TTCTTCTTCT  TCTTCTTCTT  CTTCATATCG  AAGTATAGTT      120

GACATATTGT  ATTAGATTCA  GGTGTACAGC  ATAGTGATTC  AGGTGTACAG  CATAGTGATT      180

CAACAATTAA  ATGCACTTCA  ACATTAAAAA  ATGCCTCACC  ATGTTAAGTG  TAGTTACCAT      240

CTGTCACCAT  AC                                                              252
```

( 2 ) INFORMATION FOR SEQ ID NO:2:

( i ) SEQUENCE CHARACTERISTICS:
        ( A ) LENGTH: 234 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..119
        ( D ) OTHER INFORMATION: /note= "Nucleotides 1-119 are
            unique flanking sequence"

( i x ) FEATURE:
        ( A ) NAME/KEY: misc_feature
        ( B ) LOCATION: 120..163
        ( D ) OTHER INFORMATION: /note= "Nucleotides 120-163 are
            repeat sequence"

( i x ) FEATURE:
        ( A ) NAME/KEY: misc_feature
        ( B ) LOCATION: 164..234
        ( D ) OTHER INFORMATION: /note= "Nucleotides 164-234 are
            unique flanking sequence"

( x i ) SEQUENCE DESCRIPTION: SEQ ID NO:2:

```
TTTGAACGGA  ATATTTTTAA  GTCCTGAAGA  TTTGTGAAAG  TTTAACGGTT  TAATGTCCAA       60
```

| GTGTGCAAAT | AAAAGTAAAA | TTATAAAGCA | TGCTATCTTG | TTTCCCACAG | CATTTCTAAA | 120 |
| TTTTATTTAT | TTATTTATTT | ATTTATTTAT | TTATTTATTT | ATTTACACTT | TCTAAATTTT | 180 |
| AATGACAATG | TTGTATACAG | TGAAACCTCT | CATTAATTTG | AAAAACAGCA | AAGA | 234 |

( 2 ) INFORMATION FOR SEQ ID NO:3:

( i ) SEQUENCE CHARACTERISTICS:
        ( A ) LENGTH: 279 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..111
        ( D ) OTHER INFORMATION: /note= "Nucleotides are unique
            flanking sequence"

( i x ) FEATURE:
        ( A ) NAME/KEY: misc_feature
        ( B ) LOCATION: 112..204
        ( D ) OTHER INFORMATION: /note= "Nucleotides 112-204 are
            repeat sequence"

( i x ) FEATURE:
        ( A ) NAME/KEY: misc_feature
        ( B ) LOCATION: 205..279
        ( D ) OTHER INFORMATION: /note= "Nucleotides are unique
            flanking sequence"

( x i ) SEQUENCE DESCRIPTION: SEQ ID NO:3:

| TACACAGGAA | TGAGAAGAAT | GATATGCCTG | CTGAAAACCT | TTTCAGCACT | TGAAGGGATG | 60 |
| AGCACTGGGT | GTTATACTAT | ATGTTGGCAA | ATCGAACTTC | AATAAAAAAA | AGAAGAAAGA | 120 |
| AAGAAGAAAG | AAGGAAAGAG | AAAGAAAAAG | AAAGAAAGAA | AGAAAGAAAG | AAAGAAAGAA | 180 |
| AGAAAGAAAG | AAAGAAAGAA | AGAAAACCTT | TCAAACTTCT | AGTTTGACAA | TGCAATTGTG | 240 |
| TATTAGGAAA | GGGAGTTGCA | ATATATAGAC | CTCTCCAGA | | | 279 |

( 2 ) INFORMATION FOR SEQ ID NO:4:

( i ) SEQUENCE CHARACTERISTICS:
        ( A ) LENGTH: 475 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..280
        ( D ) OTHER INFORMATION: /note= "Nucleotides 1-280 are
            unique flanking sequence"

( i x ) FEATURE:
        ( A ) NAME/KEY: misc_feature
        ( B ) LOCATION: 281..315
        ( D ) OTHER INFORMATION: /note= "Nucleotides 281-315 are
            repeat sequence"

( i x ) FEATURE:
        ( A ) NAME/KEY: misc_feature
        ( B ) LOCATION: 316..475
        ( D ) OTHER INFORMATION: /note= "Nucleotides 316-475 are
            unique flanking sequence"

( x i ) SEQUENCE DESCRIPTION: SEQ ID NO:4:

| CTTTCAGGGN | AACTCCTGCC | CTCCTGGGAG | TCCAAAGCCT | TTTCTTTTAC | CCTGATTTGT | 60 |

| CCTTTCTCAA | ATACCCAGAC | TCTAAAGTGG | CAACATTAAA | TATGCTAACT | CCATTTAAAA | 120 |
| GTGCCATTTG | AGGGCAGCCC | TGGTGGCTCA | GTGGTTTAGC | GCTGCCTACA | GCCTAGGGCG | 180 |
| TGATCCTGGA | GACCTGGGAT | TGAGTCCCAC | GTCGGGCTCC | CTGCATGGAG | CCTGCTTCTC | 240 |
| CCTCTGCCTG | TGTCTCTGCC | TCTCTCTCTG | TGTCTCTCAT | AAATAAATAA | ATAAATAAAT | 300 |
| AAATAAATAA | ATAAATCTTA | AAAAAAAAAT | AGAAGTGCCA | TTTGATGTCT | TCATCTATTG | 360 |
| ATGACTCAAT | CAAGTTTATT | ATCTACTTCA | AGTTGCTCTA | GCTGAAATCA | AGAGTCGGGA | 420 |
| CGCTCAACCA | AGTGAGCCCT | CCAGGTACCC | CACAAATGTT | GATAGTTCAA | ACTTT | 475 |

(2) INFORMATION FOR SEQ ID NO:5:

(i) SEQUENCE CHARACTERISTICS:
        (A) LENGTH: 427 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..182
        (D) OTHER INFORMATION: /note= "Nucleotides 1-182 are
            unique flanking sequence"

(ix) FEATURE:
        (A) NAME/KEY: misc_feature
        (B) LOCATION: 183..240
        (D) OTHER INFORMATION: /note= "Nucleotides 183-240 are
            repeat sequence"

(ix) FEATURE:
        (A) NAME/KEY: misc_feature
        (B) LOCATION: 241..427
        (D) OTHER INFORMATION: /note= "Nucleotides 241-427 are
            unqiue flanking sequence"

(xi) SEQUENCE DESCRIPTION: SEQ ID NO:5:

| TTTCTCCTCT | CTTCTAAGAT | GATCACTTCT | ACTCTACTGG | GATCTCTGAA | GGGGATCCCA | 60 |
| ATAATGGCAT | CCTGCTTCAT | GCAGGGGTGC | TGAACAAGTT | GAGAGATAAA | GCAACAGGCA | 120 |
| AATATGAAGG | TAAACATATC | GACTTTATCA | CTGTGGGAGG | CTAAATTGGA | GGTGTACTTT | 180 |
| GTCTTTCTCC | TTTCTTTCTT | TCTTTCTTTC | TTTCTTTCTT | TCTTTCTTTC | TTTCTTTCTT | 240 |
| TTGCTTTTTG | TTAGATTGTG | TTTATTTATT | TGAGAGAAAG | AGAGTGGAGG | GAGGGGCAGA | 300 |
| CTGAGAGGGA | GAAGTAGACT | CCATGGTGAG | CAGGGAGCCT | GATGAGACAT | GAGGCTCCAT | 360 |
| CCCAGGACCC | TGGGACCATA | ACCTGAGCTA | TTTTCTCTGA | ACAAAGGCAC | TGCTGAGGTA | 420 |
| GTTCAAG | | | | | | 427 |

(2) INFORMATION FOR SEQ ID NO:6:

(i) SEQUENCE CHARACTERISTICS:
        (A) LENGTH: 454 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..133
        (D) OTHER INFORMATION: /note= "Nucleotides 1-133 are
            unique flanking sequence"

(ix) FEATURE:

(A) NAME/KEY: misc_feature
(B) LOCATION: 134..307
(D) OTHER INFORMATION: /note= "Nucleotides 134-207 are repeat sequence"

(ix) FEATURE:
(A) NAME/KEY: misc_feature
(B) LOCATION: 308..454
(D) OTHER INFORMATION: /note= "Nucleotides 308-454 are unique flanking sequence"

(xi) SEQUENCE DESCRIPTION: SEQ ID NO:6:

| | | | | | | |
|---|---|---|---|---|---|---|
| TGCAGTTTTT | GAAGAAACTC | CTGAAATAAG | GGCAGAGACA | AGAGAGGAAG | GAGAAAGGGA | 60 |
| GGTGACCCTG | TGAACGCCTG | AACTTAATCC | TGGACAGACA | CCCCTTCCCT | GGTACTTCTA | 120 |
| TTTTTCCAAA | ACGAAAGAAA | GAAAAAAAAA | GACCAAAAAA | AGAAAAAAAG | AAAAGAAAAA | 180 |
| GAAAGAAAGA | AAGAAAGAAA | GAAAGAAAGA | AGAAAGAAA | GAAAGAAAGA | AAGAAAAAGA | 240 |
| AAGAAAGAAA | GAAAGAAAGA | AAGAAAGAAA | GAAAGAAAGA | AAGAAAGAAA | GAAAGAAAGA | 300 |
| AAGAAAAGTG | AATTAGAACT | CATTTATCTT | TGTTAACTTT | CCTCATTGTT | GGATAACTGT | 360 |
| ACCGGTGTTA | TTTAAGGAAA | TACTATTGAA | GTATGCCGGG | GAACAGGACC | ATGATGTCTA | 420 |
| CCACTTATTC | TCAAGTGGTT | TGGAGAAAAA | GAAT | | | 454 |

(2) INFORMATION FOR SEQ ID NO:7:

(i) SEQUENCE CHARACTERISTICS:
(A) LENGTH: 394 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..233
(D) OTHER INFORMATION: /note= "Nucleotides 1-233 are unique flanking sequence"

(ix) FEATURE:
(A) NAME/KEY: misc_feature
(B) LOCATION: 234..349
(D) OTHER INFORMATION: /note= "Nucleotides 234-349 are repeat sequence"

(ix) FEATURE:
(A) NAME/KEY: misc_feature
(B) LOCATION: 350..394
(D) OTHER INFORMATION: /note= "Nucleotides 350-394 are unique flanking sequence"

(xi) SEQUENCE DESCRIPTION: SEQ ID NO:7:

| | | | | | | |
|---|---|---|---|---|---|---|
| TATTAATGAT | ATTTTAGATA | GTAATTTCCA | GTTCTGCATT | CATATCAGAA | TTTAATGTTT | 60 |
| AAAAACTATA | CTGTATAAAA | ACCTGCCTTT | GTAAATGTAA | GAAAATATTG | GGTATATACT | 120 |
| TTGGATGAAT | GGATGGAGAA | GAAACTTATT | TTATATGATT | TTAAAAGTGT | AGGATTATGG | 180 |
| GAATATACAC | ATATACACTT | TGTGTGCATT | TCAGTGTTTT | TAAAACATTA | AAATTTTTCT | 240 |
| TTTTTCTTTT | TCTTTTCTTT | TCTCTCTCTC | TTTCTTTCTT | TCTTTCTTTC | TTTCTTTCTT | 300 |
| TCTTTCTTTC | TTTCTTTCTT | TCTTTCTTTC | TTTCTTTCTT | TCTTTCTTTT | GCTTGTCTTG | 360 |
| GATAGATACT | TCAATGAAGG | TCTGCATGCT | TCTA | | | 394 |

(2) INFORMATION FOR SEQ ID NO:8:

(i) SEQUENCE CHARACTERISTICS:
(A) LENGTH: 344 base pairs
(B) TYPE: nucleic acid (C) STRANDEDNESS: double
(D) TOPOLOGY: linear (ii) MOLECULE TYPE: DNA (genomic)

(ix) FEATURE:
 (A) NAME/KEY: misc_feature
 (B) LOCATION: 1..41
 (D) OTHER INFORMATION: /note= "Nucleotides 1-41 are unique flanking sequence"

(ix) FEATURE:
 (A) NAME/KEY: misc_feature
 (B) LOCATION: 42..120
 (D) OTHER INFORMATION: /note= "Nucleotides 42-120 are repeat sequence"

(ix) FEATURE:
 (A) NAME/KEY: misc_feature
 (B) LOCATION: 121..344
 (D) OTHER INFORMATION: /note= "Nucleotides 121-344 are unique flanking sequence"

(xi) SEQUENCE DESCRIPTION: SEQ ID NO:8:

| | | | | | | |
|---|---|---|---|---|---|---|
| TTAACATTCT | CTGCCTCTCC | CTTTGCCCCT | CTCACCCCTC | TAAAAAAAAA | AAAAGAAAAA | 60 |
| AGAAAGAAAG | AAAGAAAGAA | AGAAAGAAAG | AAAGAAAGAA | AGAAAGAAAG | AAAGAAAGAA | 120 |
| ACTCTAGACA | GAAGAGATTA | TCCACAAATT | GATACAATTT | GGGATATAAG | ATTGGNAGAA | 180 |
| GGTTTCCTAT | AAGAACAATA | CTAGAAAATA | TTAATATATT | TAAGGAATTC | AAAGGGAAAG | 240 |
| TTTCTAACAA | GCAATTGAAC | ACAGGTTATG | GTAACACATG | CTGGTAATTT | GTAAATTTGA | 300 |
| TTAACTGGCA | TGTTATTAGG | AATGCTTACT | TGTTTGGAGA | CTAA | | 344 |

(2) INFORMATION FOR SEQ ID NO:9:

(i) SEQUENCE CHARACTERISTICS:
 (A) LENGTH: 334 base pairs
 (B) TYPE: nucleic acid
 (C) STRANDEDNESS: double
 (D) TOPOLOGY: linear (ii) MOLECULE TYPE: DNA (genomic)

(ix) FEATURE:
 (A) NAME/KEY: misc_feature
 (B) LOCATION: 1..153
 (D) OTHER INFORMATION: /note= "Nucleotides 1-153 are unique flanking sequence"

(ix) FEATURE:
 (A) NAME/KEY: misc_feature
 (B) LOCATION: 154..269
 (D) OTHER INFORMATION: /note= "Nucleotides 154-269 are repeat sequence"

(ix) FEATURE:
 (A) NAME/KEY: misc_feature
 (B) LOCATION: 270..334
 (D) OTHER INFORMATION: /note= "Nucleotides 270-334 are unique flanking sequence"

(xi) SEQUENCE DESCRIPTION: SEQ ID NO:9:

| | | | | | | |
|---|---|---|---|---|---|---|
| TGAATTTCTA | TATATAATAG | GACTNCTTTA | AACTATGGTT | CCNAGAAAAA | TGGGGAAATN | 60 |
| CTATATATCT | CATTTTCTAG | TCCCCAGTCT | AGTTCACTGC | CCGCCTGACC | AACATCCACC | 120 |
| AGTGATAGTG | AAAAATTAAA | GAAAAACCTG | NNCAAATAAA | TAAATAAATA | AATAAATGAA | 180 |
| TGAATGAAAA | AAAGAAAGAA | AGAAAGAAAG | AAAGAAAGAA | AGAAAGAAAG | AAAGAAAGAA | 240 |
| AGAAAGAAAG | AAAGAAAGAA | AGAAAGGAAA | GAGACCTGTN | CCGAATTAAA | TCACCAGACT | 300 |
| GGGGGAGGCC | TNTCTGTGAT | ATGAAAATAA | CTGA | | | 334 |

( 2 ) INFORMATION FOR SEQ ID NO:10:

( i ) SEQUENCE CHARACTERISTICS:
        ( A ) LENGTH: 206 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..61
        ( D ) OTHER INFORMATION: /note= "Nucleotides 1-61 are unique
            flanking sequence"

( i x ) FEATURE:
        ( A ) NAME/KEY: misc_feature
        ( B ) LOCATION: 61..123
        ( D ) OTHER INFORMATION: /note= "Nucleotides 62-123 are
            repeat sequence"

( i x ) FEATURE:
        ( A ) NAME/KEY: misc_feature
        ( B ) LOCATION: 124..206
        ( D ) OTHER INFORMATION: /note= "Nucleotides 124-206 are
            unique flanking sequence"

( x i ) SEQUENCE DESCRIPTION: SEQ ID NO:10:

```
CTGTGAGATC  TCCTAAATTA  GAGGTCTAAC  CATAAAAGTT  TAGTCCTCTA  ACAACCTAAG      60

CAAAAATAAA  TAAATAAATA  AATAAATAAA  TAAATAAATA  AATAAATAAA  TAAATAAAAA     120

AAAATTTCTC  TCTAGGATTT  TCCCCTACCA  GTTTGTTGTT  TAATTCCTGG  GAGAGGAGCA     180

CATTCCCGCT  TAGNAGCACA  TTCTAG                                             206
```

( 2 ) INFORMATION FOR SEQ ID NO:11:

( i ) SEQUENCE CHARACTERISTICS:
        ( A ) LENGTH: 460 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..362
        ( D ) OTHER INFORMATION: /note= "Nucleotides 1-362 are
            unique flanking sequence"

( i x ) FEATURE:
        ( A ) NAME/KEY: misc_feature
        ( B ) LOCATION: 363..414
        ( D ) OTHER INFORMATION: /note= "Nucleotides 363-414 are
            repeat sequence"

( i x ) FEATURE:
        ( A ) NAME/KEY: misc_feature
        ( B ) LOCATION: 415..460
        ( D ) OTHER INFORMATION: /note= "Nucleotides 415-460 are
            unique flanking sequence"

( x i ) SEQUENCE DESCRIPTION: SEQ ID NO:11:

```
TGCTGTATGT  GAGGCTCCCT  CTCCCTACAA  GGCTCCTCTC  CTCTTTCCAA  GAAATCCAAA      60

TACTCATCCT  CTGAGACCCA  GCCCAAATGC  CCCCTCCTCC  AGAAAGCACT  CAGTGCAGGA     120

GTCCTGCAGG  CACGCACAGG  GGGACCCCAA  GCGAACACCT  TCAGACCTCA  CTCATGTATG     180

ACGGGTATGA  TGTCTTTGTG  GCAGGGTTAT  GACTGGGGGG  TTAACAGAGC  TCCTGTCATG     240

ATCTCAGGGT  TGTGGGATTG  AGCCCCACTC  AGGCTCCGTG  CTCAGCACCG  AGTCTGCTTG     300
```

| AGATTCTCTC | TTCCTCTCCC | TCTCCTCCTC | CCTTGTGTTC | TCTCTTTCTT | GAATGAATGA | 360 |
| ATGAAAGAAA | GAAAGAAAGA | AAGAAAGAAA | GAAAGAAAGA | AAGAAAGAAA | GAAATTTAT | 420 |
| AAGGGAAAGA | ATTTTTATAT | CATAGGGTTC | CTAGAACAGG | | | 460 |

(2) INFORMATION FOR SEQ ID NO:12:

(i) SEQUENCE CHARACTERISTICS:
        (A) LENGTH: 335 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..151
        (D) OTHER INFORMATION: /note= "Nucleotides 1-151 are
        unique flanking sequence"

(ix) FEATURE:
        (A) NAME/KEY: misc_feature
        (B) LOCATION: 152..200
        (D) OTHER INFORMATION: /note= "Nucleotide 152-200 are
        repeat sequence"

(ix) FEATURE:
        (A) NAME/KEY: misc_feature
        (B) LOCATION: 201..335
        (D) OTHER INFORMATION: /note= "Nucleotides 201-335 are
        unique flanking sequence"

(xi) SEQUENCE DESCRIPTION: SEQ ID NO:12:

| TGATTGTTCA | TGCAAAAAGT | AATTGCTCAG | CGCCTGCCAC | ATATCAAGCA | TCGCTTTGAG | 60 |
| TGCTTTTGAA | AGAATATGGA | CAAAGTCAAT | GTCCTTTGTG | AGTTTGTGAT | CTTATGCAAC | 120 |
| AACCGGTTGT | GATTTCTGGG | CCAAATTATC | CAAAAATAAA | TAAATAAATA | AATAAATAAA | 180 |
| TAAATAAATA | AATAAATAAA | AGATGTCACT | AATGACACAG | AAATGGAGGA | TAAGACTTTC | 240 |
| CTGGTCTAAA | AAAAAGATCA | AGAACAAACC | ATAATAAATG | CCAAATGTGT | CTATACTGAG | 300 |
| GTGAAGTGTA | TAATGATATG | TAACCANTCG | GAGCA | | | 335 |

(2) INFORMATION FOR SEQ ID NO:13:

(i) SEQUENCE CHARACTERISTICS:
        (A) LENGTH: 388 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..131
        (D) OTHER INFORMATION: /note= "Nucleotides 1-131 are
        unique flanking sequence"

(ix) FEATURE:
        (A) NAME/KEY: misc_feature
        (B) LOCATION: 132..235
        (D) OTHER INFORMATION: /note= "Nucleotides 132-235 are
        repeat sequence"

(ix) FEATURE:
        (A) NAME/KEY: misc_feature
        (B) LOCATION: 236..388
        (D) OTHER INFORMATION: /note= "Nucleotides 236-388 are
        unique flanking sequence"

(xi) SEQUENCE DESCRIPTION: SEQ ID NO:13:

```
TAACTCTGAA      AACAACTCAA      AGACTGGCAG      AAGAGCCTCT      CCACCTTTGA      ACATAGATGG         60

GAAACCACAC      TGAAAAGAGT      AGAAAGGGCT      AAATTGGTAT      AATCAGTGGG      GCTTAACTCC        120

AAGTTCATTT      GTTCTTTCTT      TCTTCCTTTC      TTTTCTTCT       TTCTTTCTTT      CTTTCTTTCT        180

TTCTTTCTTT      CTTTCTTTCT      TTCTTTCTTT      CTCTTTCTTT      CTTCCTTCCT      TCCTTTATTT        240

AAAGATTTTA      TTTATTTATT      TATTTATACA      TGGAGGAAGA      GGCAGAGGAG      AGGGAGAGGG        300

ATAAGCAGAC      TCTGTACTGA      ATATGGAGCC      AGAATTGAGG      GTGGATCCCT      AACCCTGGGG        360

TCAGGGACTG      AGCTATTTCC      TCTCATAA                                                          388
```

( 2 ) INFORMATION FOR SEQ ID NO:14:

( i ) SEQUENCE CHARACTERISTICS:
    ( A ) LENGTH: 348 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..21
    ( D ) OTHER INFORMATION: /note= "Nucleotides 1-21 are unique
      flanking sequence"

( i x ) FEATURE:
    ( A ) NAME/KEY: misc_feature
    ( B ) LOCATION: 22..156
    ( D ) OTHER INFORMATION: /note= "Nucleotides 22-156 are
      repeat sequence"

( i x ) FEATURE:
    ( A ) NAME/KEY: misc_feature
    ( B ) LOCATION: 157..348
    ( D ) OTHER INFORMATION: /note= "Nucleotides 157-348 are
      unique flanking sequence"

( x i ) SEQUENCE DESCRIPTION: SEQ ID NO:14:

```
TGCTCTTTGT      AAAATGACCT      GAAAGAAAGG      AAAGAAAGAA      AGAAGAAAGA      AAGAAAGAAA         60

GAAAGAAAGA      AAGAAAGAAA      GAAAGAAAGA      AAGAAAGAAA      GGAAGGAAGG      AAGGAAGGAA        120

GGAAGAAAGG      AAGAAAGAAA      GAAAGGAAGA      AAGAAAGAGT      GTGCCAAACT      GCCCTGATGT        180

CAGTAGNATC      AGTCTACATG      AAGTAATGAC      CCGAACTGAA      ACCCTAAACC      CATATGGCTA        240

GTAGAATATC      TGTGGTTAAT      AATGTTTATG      TAATCCAAAT      AAAGTTAATG      GGTTTTAGGA        300

CGATTCCCAG      GGTTAGTTAA      GGNCAANGAG      AATTAATTTG      GGATNTGA                          348
```

( 2 ) INFORMATION FOR SEQ ID NO:15:

( i ) SEQUENCE CHARACTERISTICS:
    ( A ) LENGTH: 497 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..363
    ( D ) OTHER INFORMATION: /note= "Nucleotides 1-363 are
      unique flanking sequence"

( i x ) FEATURE:
    ( A ) NAME/KEY: misc_feature
    ( B ) LOCATION: 364..406
    ( D ) OTHER INFORMATION: /note= "Nucleotides 364-406 are
      repeat sequence"

(ix) FEATURE:
  (A) NAME/KEY: misc_feature
  (B) LOCATION: 407..497
  (D) OTHER INFORMATION: /note= "Nucleotides 407-497 are unique flanking sequence"

(xi) SEQUENCE DESCRIPTION: SEQ ID NO:15:

| | | | | | |
|---|---|---|---|---|---|
| TTAAGGCATC | TGCAAAGCAG | CAAGAACACA | GCCTTAGTTT | AATACAATAA | ATTATGTTTG | 60
| CAATGAGGAA | CTTGCCTTCT | GCAGAAGGCT | GGAATCCTGT | TTAATAATTT | GTGTTTAAGA | 120
| AGGCATCAAA | TTAGAGAATG | TATTTTATTA | AAACGCACAT | GAAAATAGTC | ACTCCAAAAA | 180
| AGATTAGTGC | TGAAGGAGAT | ATATCAACAT | TTTACTTTTG | TTCCCACAGC | TCAGGTTGTG | 240
| ATCTCAGACT | CATGATATCA | AGACCCACAT | CAGGCTCTTT | GCTCAGTGCT | AAGTCTCTTT | 300
| AAGTTTCTCT | TTCCCTCTGC | TCCTCCCCAC | GTGCATACTC | TCTCTACTGT | CTTGCTCTCT | 360
| CTCAAATAAA | TAAATAAATA | AATAAATAAA | TAAATAAATA | AATAAATCTA | TCTTTAAAAA | 420
| AGTAAAGAAA | GTCATACAAA | TAAGCATCTG | AAAAGATACA | CAACATCATG | AGTCAAAAGA | 480
| ATCAATGACA | AGCCTTT | | | | | 497

(2) INFORMATION FOR SEQ ID NO:16:

(i) SEQUENCE CHARACTERISTICS:
    (A) LENGTH: 251 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: misc_feature
    (B) LOCATION: 1..131
    (D) OTHER INFORMATION: /note= "Nucleotides 1-131 are unique flanking sequence"

(ix) FEATURE:
    (A) NAME/KEY: misc_feature
    (B) LOCATION: 132..186
    (D) OTHER INFORMATION: /note= "Nucleotides 132-186 are repeat sequence"

(ix) FEATURE:
    (A) NAME/KEY: misc_feature
    (B) LOCATION: 187..251
    (D) OTHER INFORMATION: /note= "Nucleotides 187-251 are unique flanking sequence"

(xi) SEQUENCE DESCRIPTION: SEQ ID NO:16:

| | | | | | |
|---|---|---|---|---|---|
| TAGTTTGTCC | TGATTATGAC | CCACACAAAA | GCCCACGAAC | TAGCATTTGG | CTAATGTGTC | 60
| TCTCAAGCCG | GTTTGTAAC | AAATCTCCCT | CTCCTCCTCT | TTTTTTTAT | TTTTTCTGA | 120
| TGTTATTTGT | TTTTATTTAT | TTATTTATTT | ATTTATTTAT | TTATTTATTT | ATTTATTTAT | 180
| TTATTTTGAT | ATTATTTGTT | AAATAAAGAA | GTTAGGTCAT | GTGGTCTGTA | GATCTCCCCA | 240
| TTCTGGATCC | A | | | | | 251

(2) INFORMATION FOR SEQ ID NO:17:

(i) SEQUENCE CHARACTERISTICS:
    (A) LENGTH: 350 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: misc_feature (B) LOCATION: 1..109
(D) OTHER INFORMATION: /note= "Nucleotides 1-109 are unique flanking sequence"

(ix) FEATURE:
(A) NAME/KEY: misc_feature
(B) LOCATION: 110..195
(D) OTHER INFORMATION: /note= "Nucleotides 110-195 are repeat sequence"

(ix) FEATURE:
(A) NAME/KEY: misc_feature
(B) LOCATION: 196..350
(D) OTHER INFORMATION: /note= "Nucleotides 196-350 are unique flanking sequence"

(xi) SEQUENCE DESCRIPTION: SEQ ID NO:17:

| | | | | | |
|---|---|---|---|---|---|
| NTATCATNTG | GATAGAGAAT | CTGAGTCAGN | GGNGAGATAT | NAAATTTTTC | TNTGAAAAAG | 60 |
| TAGATTAGAT | CTCAGGCAGT | TACAAGCAGT | GATTAGAGTT | ATCTTATACA | AAAAAAAGA | 120 |
| AAAAAGAAA | GAAAGAAAAA | GAAGAAAGAA | AGAAAGAAAG | AAAGAAAGAA | AGAAAGAAAG | 180 |
| AAAGAAAGAA | GAAAGATAAA | ATGGNTTTGC | CAATCAGAAA | ATNTTTGCT | CAGCAGAANA | 240 |
| TAAAGAAAAA | GAGAGTCATA | GAGGNAAGCA | TTGNCGAGGT | GCACTGNTTA | GAGAATGCCT | 300 |
| AGGNCCTGAG | CCACACCCTA | CCAGGACCTA | GANGCTCCAC | CCNGGNAGGT | | 350 |

(2) INFORMATION FOR SEQ ID NO:18:

(i) SEQUENCE CHARACTERISTICS:
(A) LENGTH: 376 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..79
(D) OTHER INFORMATION: /note= "Nucleotides 1-79 are unique flanking sequence"

(ix) FEATURE:
(A) NAME/KEY: misc_feature
(B) LOCATION: 80..229
(D) OTHER INFORMATION: /note= "Nucleotides 80-229 are repeat sequence"

(ix) FEATURE:
(A) NAME/KEY: misc_feature
(B) LOCATION: 230..376
(D) OTHER INFORMATION: /note= "Nucleotides 230-376 are unique flanking sequence"

(xi) SEQUENCE DESCRIPTION: SEQ ID NO:18:

| | | | | | |
|---|---|---|---|---|---|
| TATNCCATCA | GAGAAGATAA | AGCAATTCTC | AAAAATTGGA | ATAATTGGAA | TAAGACCATA | 60 |
| AAACAACCCA | AAGACATACA | AAAAAGAGAA | AAGAAGAAAGA | AAGAAAGAAA | GAAAGAAGAA | 120 |
| AGAAAGAAAG | AAAGAAAGAA | AGAAAGAAAG | AAAGAAAGAA | GAAAGAAAGA | AAGAGAAAAA | 180 |
| GAAAAGAAA | AAGAAAAAGA | AAAAGAAAAA | GAAAAGAAAA | AGAAAAAAG | ATTCGAGGAG | 240 |
| AGATTAATGA | CTTAGAACAC | AGAAAATAGA | ATAAATAAAT | CTGGAAGCTT | CTGTTTCTTT | 300 |
| TTACACTGTC | AGGGAATATG | CCACAGACAA | GGAGAGGGGA | AGTCAATATT | TAATTCCGGA | 360 |
| ATCACAACGT | TCCCCC | | | | | 376 |

(2) INFORMATION FOR SEQ ID NO:19:

(i) SEQUENCE CHARACTERISTICS:
(A) LENGTH: 299 base pairs ( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: misc_feature
( B ) LOCATION: 1..128
( D ) OTHER INFORMATION: /note= "Nucleotides 1-128 are
unique flanking sequence"

( i x ) FEATURE:
( A ) NAME/KEY: misc_feature
( B ) LOCATION: 129..199
( D ) OTHER INFORMATION: /note= "Nucleotides 129-199 are
repeat sequence"

( i x ) FEATURE:
( A ) NAME/KEY: misc_feature
( B ) LOCATION: 200..299
( D ) OTHER INFORMATION: /note= "Nucleotides 200-299 are
unique flanking sequence"

( x i ) SEQUENCE DESCRIPTION: SEQ ID NO:19:

| | | | | | | |
|---|---|---|---|---|---|---|
| TCAGGTCATG | ATCTCAGGTT | TGTGAGATCG | AGCCCCAATG | TCGAATTCCA | TGGTGAACGT | 60 |
| GGAACCTGCT | TAAGATTCTC | TTGCTCTCCC | TCTCTCACTG | NCCCACCCTG | TTCGCATGCT | 120 |
| CTCCCTCTGA | AAGAAAGAAA | GAAAGAAAGA | AAGAAAGAAA | GAAAGAAAGA | AAGAAAGAAA | 180 |
| GAAAGAAAGA | AAGAAAAAAG | AGTAAGTATA | GACCTAGAAA | ACGAGATTCC | TATTCCACTT | 240 |
| TCATTATGGT | ATGGAGAAGT | TCAGTCCCTT | AGGGGTAAAG | TTTGTCTTTG | GGAGGCTGA | 299 |

( 2 ) INFORMATION FOR SEQ ID NO:20:

( i ) SEQUENCE CHARACTERISTICS:
( A ) LENGTH: 475 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: misc_feature
( B ) LOCATION: 1..366
( D ) OTHER INFORMATION: /note= "Nucleotides 1-366 are
unique flanking sequence"

( i x ) FEATURE:
( A ) NAME/KEY: misc_feature
( B ) LOCATION: 367..438
( D ) OTHER INFORMATION: /note= "Nucleotides 367-438 are
repeat sequence"

( i x ) FEATURE:
( A ) NAME/KEY: misc_feature
( B ) LOCATION: 439..475
( D ) OTHER INFORMATION: /note= "Nucleotides 439-475 are
repeat sequence"

( x i ) SEQUENCE DESCRIPTION: SEQ ID NO:20:

| | | | | | | |
|---|---|---|---|---|---|---|
| TGATAACCAG | GGAGGAAATT | GAAGCAATCA | TCAAAAACTT | CCAAGACACA | AAGTCCAGGG | 60 |
| NCAGATGGCT | TCCCAGGGGA | ATTCTATCAA | ATGTTTATAG | AAGAAACAAT | ACCTACTCTC | 120 |
| TTATTTTTTT | TATATTTTAA | AATATTGCAA | TAAATATTAC | TTTGTTACTG | AGGTGTCTTT | 180 |
| TTTTATTGTT | GTTGTTGTTG | TTGTTGTTGT | TGTTGTTGTT | GTTGTNNTGA | CATCGCCTCC | 240 |
| AAAACGAAGA | CTTCACTTGC | TTCATCTTAA | TTCTGGGTTN | GTGATATTTG | GNCCCCAGAT | 300 |
| TAAATTTAAA | AATGCTGAAT | AAATTTCTAA | ATCACAGCCC | TTGAATATGA | ACAATGACAC | 360 |
| TGTATCAAGG | GAAGGAAGGA | AGGAAGGAAG | GAAGGAAGGA | AGGAAGGAAG | GAAGGAAGGA | 420 |

AGGAAGGAAA GAAGGAAGGC AGAGGGAGGG AGCATAGGCA GTTAGAGAGG AAGGA                475

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CACTTCTCAT ACCCAGACTC                20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

ATGAGCACTG GGTGTTATAC                20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ATCCTGGAGA CCTGGGATTG                20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TATCGACTTT ATCACTGTGG                20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

ACGCCTGAAC TTAATCCTGG                20

(2) INFORMATION FOR SEQ ID NO:26:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:26:

GCTATCTTGT TTCCCACAGC 20

(2) INFORMATION FOR SEQ ID NO:27:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:27:

CCTGCCTTTG TAAATGTAAG 20

(2) INFORMATION FOR SEQ ID NO:28:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:28:

ATTCTCTGCC TCTCCCTTTG 20

(2) INFORMATION FOR SEQ ID NO:29:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:29:

TCTAGTCCCC AGTCTAGTTC ACTGCCC 27

(2) INFORMATION FOR SEQ ID NO:30:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:30:

CCTAAATTAG AGGTCTAACC 20

(2) INFORMATION FOR SEQ ID NO:31:

(i) SEQUENCE CHARACTERISTICS:
    (A) LENGTH: 20 base pairs
    (B) TYPE: nucleic acid
    (C) STRANDEDNESS: single (D) TOPOLOGY: linear (ii) MOLECULE TYPE: DNA (genomic)

(xi) SEQUENCE DESCRIPTION: SEQ ID NO:31:

CTCAGCACCG AGTCTGCTTG                                                        20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

AACCGGTTGT GATTTCTGGG                                                        20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

TGGGGCTTAA CTCCAAGTTC                                                        20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

GCTCTTTGTA AAATGACCTG                                                        20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

TTTGCTCAGT GCTAAGTCTC                                                        20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CTAATGTGTC TCTCAAGCCG                                                                                      20

( 2 ) INFORMATION FOR SEQ ID NO:37:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GTAGATTAGA TCTCAGGCAG                                                                                      20

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

GAGAAGATAA AGCAATTCTC                                                                                      20

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

GTGGAACCTG CTTAAGATTC                                                                                      20

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

GCCCTTGAAT ATGAACAATG                                                                                      20

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

CAATATGTCA ACTATACTTC                                                                                      20

( 2 ) INFORMATION FOR SEQ ID NO:42:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:42:

ACACAATTGC ATTGTCAAAC     20

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

GATTGAGTCA TCAATAGATG     20

( 2 ) INFORMATION FOR SEQ ID NO:44:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

ATGGAGCCTC ATGTCTCATC     20

( 2 ) INFORMATION FOR SEQ ID NO:45:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

ACAGTTATCC AACAATGAGG     20

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

TCACTGTATA CAACATTGTC     20

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:47:

CTTCATTGAA GTATCTATCC　　　　　　　　　　　　　　　　　　　　　　　　　　　　20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

TGTGGATAAT CTCTTCTGTC　　　　　　　　　　　　　　　　　　　　　　　　　　　　20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

AGTCTGGTGA TTTAATTCGG　　　　　　　　　　　　　　　　　　　　　　　　　　　　20

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

TAAGCGGGAA TGTGCTCCTC　　　　　　　　　　　　　　　　　　　　　　　　　　　　20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

CCTGTTCTAG GAACCCTATG　　　　　　　　　　　　　　　　　　　　　　　　　　　　20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

TCTGTGTCAT TAGTGACATC 20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

CAGTACAGAG TCTGCTTATC 20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

TGGGAATCGT CCTAAAACCC 20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

GACTCATGAT GTTGTGTATC 20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

TGGGGAGATC TACAGACCAC 20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

TAGGTCCTGG TAGGGTGTGG 20

(2) INFORMATION FOR SEQ ID NO:58:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:58:

AAGTCATTAA TCTCTCCTCG                                                       20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

CTAAGGGACT GAACTTCTCC                                                       20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

TCCTCTCTAA CTGCCTATGC                                                       20